US008229681B2

(12) United States Patent
Minnaar et al.

(10) Patent No.: US 8,229,681 B2
(45) Date of Patent: Jul. 24, 2012

(54) METHOD TO MEASURE TEARING RESISTANCE

(75) Inventors: Karel Minnaar, Houston, TX (US); Paulo C. Gioielli, Houston, TX (US); Mario L. Macia, Bellaire, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 422 days.

(21) Appl. No.: 12/525,496

(22) PCT Filed: Feb. 8, 2008

(86) PCT No.: PCT/US2008/001676
§ 371 (c)(1),
(2), (4) Date: Jul. 31, 2009

(87) PCT Pub. No.: WO2008/115320
PCT Pub. Date: Sep. 25, 2008

(65) Prior Publication Data
US 2010/0005864 A1      Jan. 14, 2010

Related U.S. Application Data

(60) Provisional application No. 60/918,999, filed on Mar. 20, 2007.

(51) Int. Cl.
*G06F 19/00* (2011.01)
*G06F 17/40* (2006.01)
(52) U.S. Cl. ............. 702/33; 73/799; 73/866; 702/43; 702/187; 702/189

(58) Field of Classification Search ........... 73/87, 432.1, 73/760, 788, 794, 795, 796, 799, 808, 812, 73/813, 814, 815, 818, 826, 841, 847, 849, 73/865.8, 865.9, 866; 702/1, 33, 34, 35, 702/41, 42, 43, 108, 113, 127, 182, 187, 702/189; 703/1; 708/100, 105, 131, 160, 708/200
See application file for complete search history.

(56) References Cited

U.S. PATENT DOCUMENTS 3,003,351 A * 10/1961 Ziegler et al. .................. 73/597
3,234,783 A *  2/1966 Hanson ........................ 73/797
(Continued)

FOREIGN PATENT DOCUMENTS
EP          1 621 862 A2    2/2006
(Continued)

OTHER PUBLICATIONS

Shen, G. et al., "Constraint Effects on Linepipe Toughness", 4$^{th}$ Pipeline Technology Int'l Conference, May 9-13, 2004, pp. 703-720, Ostend, Belgium.

(Continued)

*Primary Examiner* — Edward Cosimano
(74) *Attorney, Agent, or Firm* — ExxonMobil Upstream Research Company-Law Department

(57) ABSTRACT

At least one method, structure and apparatus used to measure tearing resistance of a commercial member. The method includes the use of full-scale testing methods and apparatuses to obtain unloading compliance measurements, which are used to generate a tearing resistance curve that includes the effects of geometry and considers data beyond the yield point of the commercial member. The commercial member may be a pipeline for carrying hydrocarbons.

55 Claims, 13 Drawing Sheets

U.S. PATENT DOCUMENTS

| | | | |
|---|---|---|---|
| 3,983,745 A | | 10/1976 | Juusola |
| 4,299,120 A | * | 11/1981 | Barker ............................. 73/87 |
| 4,677,855 A | * | 7/1987 | Coffin et al. .................... 73/799 |
| 4,764,882 A | * | 8/1988 | Braschel et al. ................ 702/42 |
| 4,836,029 A | * | 6/1989 | Skala et al. ..................... 73/799 |
| 4,875,170 A | * | 10/1989 | Sakurai et al. .................. 702/34 |
| 5,005,423 A | | 4/1991 | Poormon |
| 5,319,983 A | | 6/1994 | Brown et al. |
| 5,673,203 A | | 9/1997 | Annigeri et al. |
| 5,826,213 A | | 10/1998 | Kennefick |
| 6,172,511 B1 | | 1/2001 | Nicholls et al. |
| 6,778,916 B2 | | 8/2004 | Lee |
| 7,013,224 B2 | | 3/2006 | Landry et al. |
| 2006/0025937 A1 | | 2/2006 | Gao et al. |

FOREIGN PATENT DOCUMENTS

WO    WO 2008/115323 A1    9/2008

OTHER PUBLICATIONS

Timmins, P.F., "Measurements, Calculations Keys to Use", Oil & Gas Journal, May 3, 1982, pp. 266-276, v. 80, No. 18.

Wang, Y. et al., "A Quantitative Approach to Tensile Strain Capacity of Pipelines", 6$^{th}$ Int'l. Pipeline Conf., Sep. 25-29, 2006, pp. 1-8, Calgary, Alberta, Canada.

Wilkowski G.M., et al., "A Plastic Fracture Mechanics Prediction of Fracture Instability in a Circumferentially Cracked Pipe in Bending—Part II: Experimental Verification on a Type 304 Stainless Steel Pipe", Journal of Pressure Vessel Technology, Nov. 1981, pp. 359-365, v. 103, No. 4.

Zahoor, A. et al., "A Plastic Fracture Mechanics Prediction of Fracture Instability in a Circumferentially Cracked Pipe in Bending—Part 1: J-Integral Analysis", Journal of Pressure Vessel Technology, Nov. 1981, pp. 352-358, v. 103, No. 4.

Zhu, X.K. et al., "Bending Modified J-Q Theory and Crack-Tip Constraint Quantification", Int'l. Journal Fract., 2006, pp. 115-134, v. 141.

EP Search Report No. 115311, Nov. 3, 2007, 6 pages.

Anderson, T.L., "Elastic-Plastic Fracture Mechanics", *Fracture Mechanics, Fundamentals and Applications*, 1995, pp. 117-204, 2$^{nd}$ Edition, Chapter 3 and Appendix 3, CRC Press, Inc., Boca Raton, FL.

Bazant, Z.P., "Rock Fracture Via Strain-Softening Finite Elements", Journal Eng. Mechanics, American Society Civil Eng., Jul. 1984, pp. 1015-1035, v. 110, No. 7.

Cravero, S. et al., "A Constraint-Based FAD Procedure for Defect Assessments of Pipelines", 2006 ASME Pressure Vessels and Piping Div. Conference, Jul. 23-27, 2006, pp. 469-477, Vancouver BC, Canada.

Cravero, S. et al., "Evaluation of Crack Growth Resistance Curves for Pipeline Steels Using Constraint Designed Fracture Specimens", 6$^{th}$ Int'l. Pipeline Conference, Sep. 25-29, 2006, pp. 969-978, Calgary, AB, Canada.

Dotta, F. et al., "Structural Integrity Assessments of High Pressure Pipelines with Axial Flaws Using a Micromechanics Model", Int'l. Journal of Pressure Vessels and Piping, 2004, pp. 761-770, v. 81.

Jayadevan, K.R. et al., "Numerical Investigation of Ductile Tearing in Surface Cracked Pipes Using Line-Springs", Int'l. Journal of Solids and Structures, 2006, pp. 2378-2397, v. 43.

Kumar, D.V., et al., "Cyclic Tearing and Crack Growth in Circumferentially Cracked Straight Pipes", Fatigue Fract. Eng. Material Structure, 2004, pp. 1061-1072, v. 27.

Martin, G. et al., "Experimental Four Points Bending Test on a Real Size Bimetallic Welded Pipe: European Project Adimew", American Society of Mechanical Engineers, Jul. 25-29, 2004, pp. 11-19, v. 475, San Diego, CA.

Ostby, E., "Fracture Control—Offshore Pipelines. New Strain-Based Fracture Mechanics Equations Including the Effects of Biaxial Loading, Mismatch and Misalignment", 24$^{th}$ Int'l. Conf. on Offshore Mechanics & Arctic Eng., Jun. 12-17, 2005, pp. 649-658, Halkidiki, Greece.

BS-7448 Part 1—British Standard—Fracture mechanics toughness tests—*Part 1: Method for determination of $K_{Ic}$, critical CTOD and critical J values of metallic materials*; Incorporating Amendment No. 1 and Corrigendum No. 1.; Feb. 2002.

BS-7448 Part 2—British Standard—Fracture mechanics toughness tests—*Part 2: Method for determination of $K_{Ic}$, critical CTOD and critical J values of metallic materials*; Incorporating Amendment No. 1 and Corrigendum No. 1.; Aug. 1997.

BS-7448 Part 3—British Standard—Fracture mechanics toughness tests—*Part 3: Method for determination of fracture toughness of metallic materials at rates of increase in stress intensity factor greater than 3.0 MP $a \cdot m^{0.5}$ $S^{-1}$* Incorporating Amendment No. 1 and Corrigendum No. 1.; Mar. 2005.

BS-7448 Part 4—British Standard—Fracture mechanics toughness tests—*Part 4: Method for determination of fracture resistance curves and initiation values for stable crack extension in metallic material*, Incorporating Amendment No. 1 and Corrigendum No. 1.; Jul. 2001.

Designation: E-1820-06; Standard Test Method for Measurement of Fracture Toughness; Jul. 2006.

\* cited by examiner

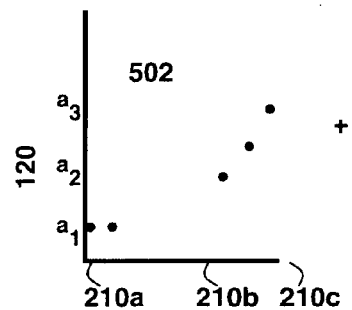
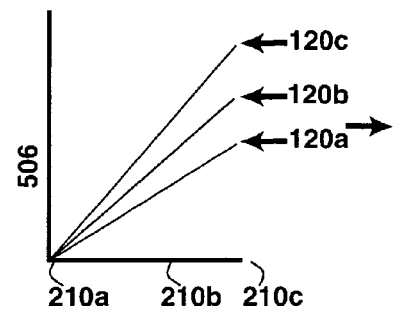
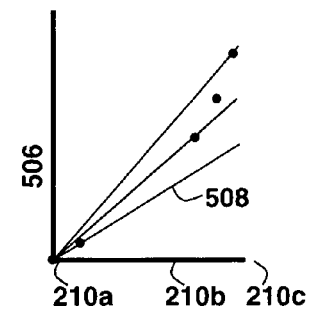
FIG. 5A  FIG. 5B  FIG. 5C
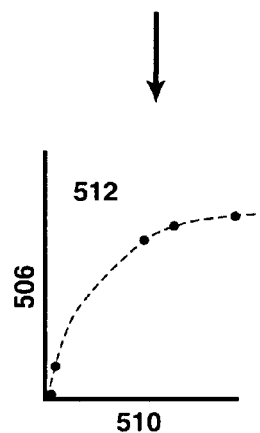
FIG. 5D

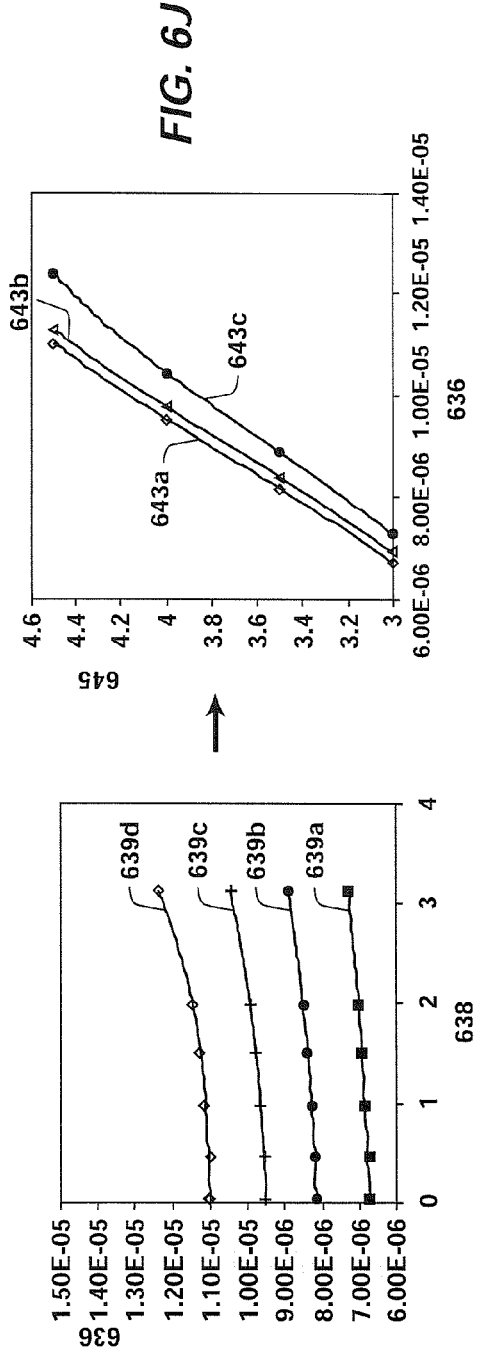
FIG. 6I
FIG. 6J
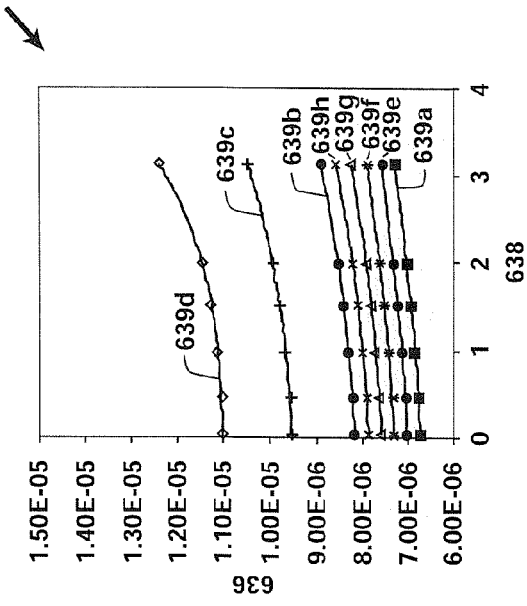
FIG. 6K

METHOD TO MEASURE TEARING RESISTANCE

CROSS REFERENCE TO RELATED APPLICATIONS

This application claims the benefit of U.S. Provisional Application No. 60/918,999, filed Mar. 20, 2007.

This application is related to U.S. Provisional Application No. 60/919,053 titled "A Framework to Determine the Capacity of A Structure," filed Mar. 20, 2007.

FIELD OF THE INVENTION

The present invention generally relates to pipeline failure prediction. More particularly, the present invention relates to methods of measuring the tearing resistance of pipelines to enhance pipeline performance predictability under high strain conditions.

BACKGROUND

This section is intended to introduce the reader to various aspects of art, which may be associated with exemplary embodiments of the present invention, which is described and/or claimed below. This discussion is believed to be helpful in providing the reader with information to facilitate a better understanding of particular aspects of the present invention. Accordingly, it should be understood that these statements are to be read in this light, and not necessarily as admissions of prior art.

The production of hydrocarbons, such as oil and gas, has been performed for numerous years. To produce these hydrocarbons, one or more wells of a field are typically drilled into a subsurface location, which is generally referred to as a subterranean formation, basin or reservoir. From the wells, lines or pipelines are utilized to carry the hydrocarbons to a surface facility for processing or from surface facility to other locations. These pipelines are typically formed from pipe segments that are welded together at weld joints to form a continuous flow path for various products. As such, these pipelines provide a fluid transport system for a wide variety of products, such as oil, gas, water, coal slurry, etc.

Generally, pipelines may be affected by various forces that damage or rupture the pipeline. Recently, increased demand for oil and gas has provided a significant incentive to place pipelines in geographic regions with large ground deformations. Placing pipelines in these regions presents engineering challenges in pipeline strength and durability that were not previously appreciated or approached. These large ground deformations may occur in seismic regions, such as around fault lines, or in arctic regions. In these regions, pipelines may be subjected to large upheaval or subsidence ground movements that occur from the ground freezing/thawing and/or large horizontal ground movements that occur from earthquake events. Because of the ground movements, pipelines, which may be above or below ground, are subject to large strains and plastic deformation that may disrupt the flow of fluids. Further, various load conditions, such as force-controlled load conditions, may be applied to the pipeline as internal pressures and external pressures. In particular, if the pipeline is subjected to predominantly force-controlled load conditions, an allowable stress design methodology is utilized to ensure that the level of stress in the pipeline remains below the yield strength of the pipeline material.

In addition, because the pipe segments are welded together, the weld joints between the pipe segments or between the pipe segments and auxiliary components, such as elbows or flanges, may provide weak points that are susceptible to these forces. For instance, a weld joint between two pipe segments may have flaws that weaken the pipeline. If the weld joint has flaws, then the pipeline may fail at the weld joint due to load conditions or ground movement. Accordingly, the weld joints of the pipe segments may be designed to have sufficient strength and fracture toughness to prevent failure of the weld joint under large strains. This may be accomplished by selecting a proper weld and pipeline material and geometry and selecting an appropriate welding technique, inspection acceptance criteria, and geometry.

To make such determinations about welds and materials, objective inputs may be used. For instance, one such input is the measurement of tearing resistance. Tearing resistance represents the strength of the crack tip as function of the crack size. Tearing resistance is typically represented as a curved line, evincing the material strengthening while it tears. Typically, tearing resistance curves have been obtained based on a single fracture parameter such as crack tip opening displacement (CTOD) or J-integral. ANDERSON, T. L., *Fracture Mechanics: Fundamentals and Applications*, 2d ed., CRC Press, Inc. (1995). These parameters are usually measured using geometry-independent specimens. However, at large-scale yielding, the geometry-independent specimens are not valid and geometry-dependent analysis is preferred.

Attempts to more accurately measure tearing resistance at large scale yielding include applying a multiplying factor to increase the measured tearing resistance. Unfortunately, under large scale plasticity the tearing resistance is a function of the geometry and the multiplying factor is an unknown variable. WANG, Y; LIU, M; HORSLEY D; ZHOU, J; "A Quantitative Approach to Tensile Strain Capacity of Pipelines," IPC2006-10474 (September 2006). A second approach utilizes non-standard specimens, such as Single Edge Notch Tension (SENT) to estimate tearing resistance at large scale yielding. ØSTBY E.; "Fracture control—Offshore pipelines: New strain-based fracture mechanics equations including the effects of biaxial loading, mismatch and misalignment;" 24th Int. Conference on Offshore Mech.'s and Arctic Eng'g; paper OMAE2005-67518, ASME; Halkidki, Greece (June 2005). However, these specimens tend to overestimate the tearing resistance by a variable factor. Some standard methods for determining tearing resistance are described in ASTM E 1820-06, "Standard Test Method for Measurement of Fracture Toughness," ASTM Int'l; and BS 7448 (parts 1-4), "Fracture Mechanics Toughness Test," British Standards Institute.

Accordingly, the need exists for a method and apparatus that may be utilized to measure tearing resistance that includes the effects of the geometry of the member being tested and the effect of plastic strain on the tearing resistance.

SUMMARY OF INVENTION

One embodiment of the present invention is disclosed as a method of obtaining a representative tearing resistance curve of a commercial member. The method includes conducting a full scale fracture mechanics test of a specimen having a specimen geometry of a representative size and shape of the commercial member and at least one specimen flaw having a specimen flaw geometry of a representative size and shape of a flaw in the commercial member, wherein the full scale fracture mechanics test provides at least two results; and generating a tearing resistance curve of the specimen utilizing the at least two results of the full scale fracture mechanics test, wherein the tearing resistance curve of the specimen is representative of a tearing resistance curve of the commercial member and is dependent upon at least the size and shape of the specimen geometry and the size and shape of the specimen flaw geometry. In one embodiment the full scale fracture mechanics test includes loading the specimen past the specimen's yield point and may include cyclical loading of the specimen. In further embodiments, the specimen may include a weld having a geometry representative of the commercial member. Further, the commercial member may be a pipe segment and the loading may be bending, torsional, compressive or some combination.

Another embodiment of the present invention is disclosed as a method of producing hydrocarbons. The method includes designing a pipeline for producing hydrocarbons. The pipeline comprises a commercial pipe segment, wherein the commercial pipe segment is selected utilizing a representative tearing resistance curve of the commercial pipe segment. Obtaining the representative tearing resistance curve of the commercial pipe segment includes conducting a full scale fracture mechanics test of a specimen having a specimen geometry of a representative size and shape of the commercial pipe segment and at least one specimen flaw, the specimen flaw having a specimen flaw geometry of a representative size and shape of a flaw in the commercial pipe segment, wherein the full scale fracture mechanics test provides at least two results; and generating a tearing resistance curve of the specimen utilizing the at least two results of the representative fracture mechanics test, wherein the tearing resistance curve of the specimen is representative of a tearing resistance curve of the commercial pipe segment and is dependent upon at least the size and shape of the specimen geometry and the size and shape of the specimen flaw geometry. The method further includes producing hydrocarbons using the pipeline.

A third embodiment of the present invention is disclosed as a structure. The structure includes a commercial member, wherein the commercial member is selected utilizing a representative tearing resistance curve of the commercial member. Obtaining the representative tearing resistance curve of the commercial member includes conducting a full scale fracture mechanics test of a specimen having a specimen geometry of a representative size and shape of the commercial member and at least one specimen flaw, the specimen flaw having a specimen flaw geometry of a representative size and shape of a flaw in the commercial member, wherein the full scale fracture mechanics test provides at least two results; and generating a tearing resistance curve of the specimen utilizing the at least two results of the representative fracture mechanics test, wherein the tearing resistance curve of the specimen is representative of a tearing resistance curve of the commercial member and is dependent upon at least the size and shape of the specimen geometry and the size and shape of the specimen flaw geometry.

A fourth embodiment of the present invention is disclosed as an apparatus having a processor and a memory coupled to the processor. The processor is configured to execute computer readable instructions to calculate a measured compliance of a specimen from at least two test results, wherein the test results are obtained by conducting a full scale fracture mechanics test of the specimen having a specimen geometry of a representative size and shape of a commercial member and at least one specimen flaw, the specimen flaw having a specimen flaw geometry of a representative size and shape of a flaw in the commercial member. The computer readable instructions are further configured to develop at least one transfer function between the measured compliance of the specimen and an at least one specimen flaw height; utilize the at least one transfer function to calculate a fracture driving force of the specimen as a function of strain of the specimen; and plot the fracture driving force as a function of change in the at least one specimen flaw height to determine a tearing resistance curve of the specimen.

A fifth embodiment of the present invention is disclosed as a method of obtaining a tearing resistance curve of a commercial member. The method includes obtaining at least two results from a full scale fracture mechanics test of a specimen having a specimen geometry of a representative size and shape of the commercial member and at least one specimen flaw, the specimen flaw having a specimen flaw geometry of a representative size and shape of a flaw in the commercial member, wherein the full scale fracture mechanics test includes; calculating a measured compliance of the specimen utilizing the at least two results from the full scale fracture mechanics test; and developing at least one transfer function between the measured compliance of the specimen and the at least one specimen flaw height, wherein the at least one transfer function utilizes at least one compliance measurement from past the yield point of the specimen.

BRIEF DESCRIPTION OF THE DRAWINGS

The foregoing and other advantages of the present disclosure may become apparent upon reading the following detailed description and upon reference to the drawings in which:

FIGS. 5A-5D are illustrations of exemplary graphical representations of numerical analyses used to calculate a tearing resistance curve in accordance with certain aspects of the present invention.

DETAILED DESCRIPTION

Figure 1A:
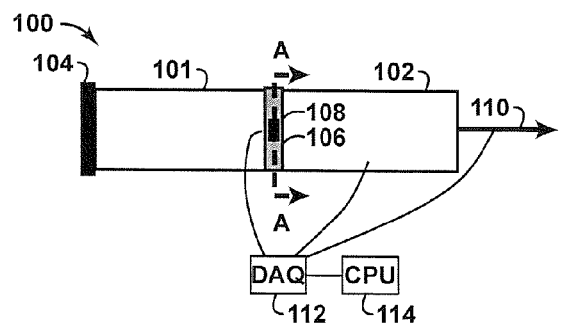
FIGS. 1A-1C are illustrations of various aspects of an exemplary experimental configuration in accordance with certain aspects of the present invention.

In the following detailed description, the specific embodiments of the present invention will be described in connection with its preferred embodiments. However, to the extent that the following description is specific to a particular embodiment or a particular use of the present invention, this is intended to be illustrative only and merely provides a concise description of the exemplary embodiments. Accordingly, the invention is not limited to the specific embodiments described below, but rather, the invention includes all alternatives, modifications, and equivalents falling within the true scope of the appended claims.

The present invention is directed to a method of measuring the tearing resistance of a commercial member. More particularly, the present method may be used to measure the tearing resistance of a welded pipe member submitted to plastic deformation. Some embodiments of the present invention comprise conducting a full scale fracture mechanics test of a specimen having a flaw to generate a tearing resistance curve that is dependent on the geometry of the specimen, the geometry of the flaw, and the geometry of the weld, if any, wherein the geometry of the specimen is representative of the geometry of the commercial member For purposes of the present disclosure "tearing resistance" is defined as a measure of the material resistance to crack growth. Those who are skilled in the art will recognize that tearing resistance is characterized as a measure of a fracture driving force versus a measure of flaw or crack geometry. Some examples include: crack tip opening displacement (CTOD), J-integral, crack mouth opening displacement (CMOD), or crack tip opening angle (CTOA) versus change in crack height.

The term "commercial member" refers to a part or all of a full scale structure that may be used in a full size, commercially viable application. For instance, the commercial member of a pipeline may be a single commercial grade pipe segment, two commercial grade pipe segments bonded together end-to-end (e.g. welded), or a pipeline made up of numerous pipe segments bonded together. The commercial member may also be a discrete part of a structure, such as a support beam or a portion of the support beam from a lattice structure. The commercial member may also comprise a variety of cross-sectional geometries, such as circular, I-beam, square, or others.

The term "full scale" means the specimen and the specimen flaw (and, if applicable, the specimen weld) have a size and shape representative of the size and shape of a commercial member with a flaw such that the tearing resistance curve of the specimen is representative of the tearing resistance curve of the commercial member. The term "full scale" excludes testing specimens such as single-edge notch bend (SENB), single-edge notch tension (SENT), compact (C(T)), and disk-shaped compact (DC(T)). As an example, for a pipe segment, the whole pipe may be tested, or a half or a quarter of the pipe may be sufficient to obtain the tearing resistance curve in accordance with the teachings of the present invention.

The term "fracture mechanics test" means conducting a test of a specimen to measure the mechanical response of the specimen in the presence of a flaw. More specifically, it means applying a load to the specimen to measure the response, wherein the load may be one of tension, torsion, bending, compression, or some combination thereof. The fracture mechanics test may include submitting the specimen to loads beyond the yield point of the specimen to obtain data from the plastic response of the specimen.

At least one embodiment of the present invention comprises: conducting at least one full scale fracture mechanics test of a member having a flaw in combination with an unloading compliance method to determine a tearing or crack growth resistance curve. The unloading compliance method is one exemplary method to develop the tearing resistance curve. An explanation of one embodiment of the unloading compliance method may be found in CRAVERO, SEBASTIAN; RUGGIERI, CLAUDIO; *Evaluation of Crack Growth Resistance Curves for Pipeline Steels Using Constrain Designed Fracture Specimens*; IPC2006-10075 (September 2006). The unloading compliance method generally involves using a first numerical simulation model to develop transfer functions between a measured compliance of the member and the height of the flaw, which may be used to calculate a fracture driving force (the force available to increase the cracked surface area) as a function of strain; then combining the test results and numerical simulation output to determine a tearing resistance curve. Note that some embodiments of the present invention may utilize non-linear material behavior to develop transfer functions to determine crack growth from compliance measurements. Specifically, load-displacement ratios beyond the yield point of the specimen may be used to develop the transfer functions. The tearing resistance curve may be represented by a plot of crack tip opening displacement (CTOD), J-integral, crack mouth opening displacement (CMOD), or crack tip opening angle (CTOA) versus change in crack height (or crack growth). Other methods and/or systems for measuring tearing resistance may include inferring changes in crack height from changes in electrical resistivity or potential drop across the crack.

Figure 1B:
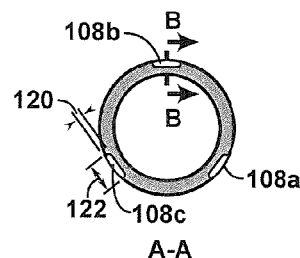
Figure 1C:
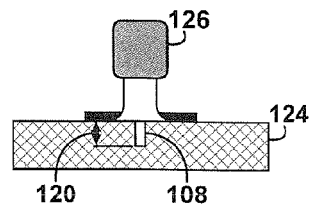

Turning now to the drawings, and referring initially to FIGS. 1A-1C, an exemplary experimental or test configuration 100 in accordance with certain aspects of the present invention is illustrated. In FIG. 1A, a top view of a first pipe specimen 101 and a second pipe specimen 102 in an exemplary experimental configuration 100 is shown. Note that the pipe specimens are "members" and the use of the term "pipe specimen" here is merely exemplary. The first pipe specimen 101 is fixed at one end 104 and welded to the second pipe specimen 102 at the other end with a weld 106 and an arrow shows the direction of an applied tensile load 110. The weld 106 includes at least one flaw 108a-108n, wherein "n" may be any integer and a single flaw or reference to flaws generally may be referred to as 108. The exemplary configuration 100 may further include a data acquisition device (DAQ) 112 to receive data input from the first and second pipe specimens 101, 102 and coupled to a processing device 114, such as a computer, server, database or other processor-based device. FIG. 1B shows an exemplary cross-sectional view A-A of the first and second pipe segments 101, 102 at the location of the weld 106 showing the flaw height 120 and flaw length 122. Although three flaws 108a-108c are shown, the number of flaws may vary significantly depending upon the type of welding process and material used, the pipe material and size used, and other factors. FIG. 1C shows a cross-section view B-B of flaw 108b in the pipe wall 124, the flaw height 120, and a tool 126 for measuring the flaw or crack mouth opening displacement (CMOD). Each flaw 108a-108c may have a corresponding flaw height 120a-120c. Note, the tool 126 may be a clip gauge or other measurement tool capable of measuring the CMOD.

When referencing FIGS. 1A-1C, it should be noted that although only two pipe specimens 101, 102 are shown, the present invention may include only one pipe specimen or more than two pipe specimens. Also note that the first and second pipe specimens 101, 102 are preferably the same geometry (e.g. the same diameter and wall thickness) and comprised of the same material, but a person of skill in the art recognizes that different pipe geometry and materials may be used within the scope of the present invention. The first and second pipe specimens 101, 102 may be selected to have the same geometry and material as pipes intended to be commercially used in a pipeline for carrying hydrocarbons and other liquids into and out of a wellbore drilled for purposes of hydrocarbon production. Also, the specimens used need not be "complete" specimens, but preferably include enough of the geometry of the pipe or member, flaw, and weld (if applicable) to obtain results that are dependent upon the geometry of the pipe or member, flaw, and weld. Also note that the present invention may further be applied to other types of members where a measure of tearing resistance may be beneficial, such as pipelines used for utility service or structural members such as I-beams.

The flaws 108 of FIGS. 1A-1C may be formed by machining or other means in the circumference of the pipe body 101, 102 or in the girth weld 106 joining two or more pipe segments to establish a lower bound tearing resistance response. The flaws are preferably shaped and located to accurately reflect the shape and location of flaws occurring in a commercial application of the member. The tool 126 is attached to each flaw 108 to measure the CMOD of each flaw 108. The change in flaw or crack height 120 of each flaw or crack 108 is measured as the applied load 110 is increased. Crack growth history may be measured in some embodiments of the present invention and may be used in combination with finite element analysis to measure a tearing resistance curve of the pipe and weld (in cases where there is a weld) material.

Figure 2A:
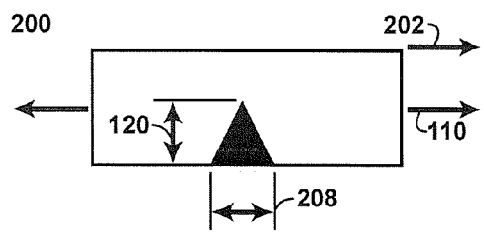
FIGS. 2A-2D are illustrations of exemplary graphical representations of numerical analyses relating to a physical model as disclosed in FIGS. 1A-1C or a computer model.
Figure 2B:
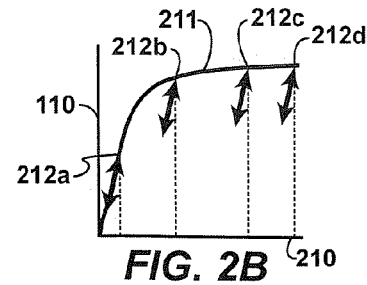
Figure 2C:
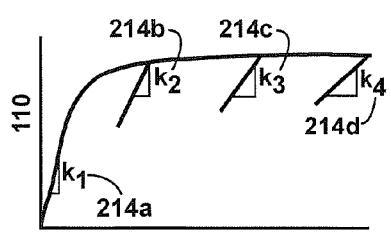
Figure 2D:
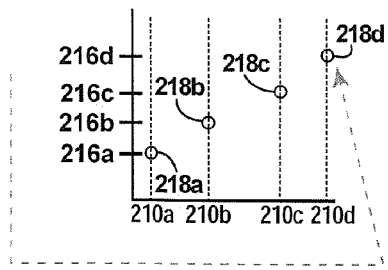

Referring now to FIGS. 2A-2D, showing illustrations of exemplary graphical representations of numerical analyses relating to a physical model as disclosed in FIGS. 1A-1C or a computer model. Accordingly, FIGS. 2A-2D may be best understood by concurrently viewing FIGS. 1A-1C. FIG. 2A illustrates a portion of an exemplary specimen 200 showing displacement 202, load 110, flaw height 120, and crack mouth opening displacement (CMOD) 208. FIG. 2B illustrates a graph of load 110 versus strain 210 and shows a plurality of points of cycling 212a-212d, which may be referred to as 212. A point of cycling 212 is a point on the graph where the specimen 200 is unloaded, then reloaded. In some embodiments, the loading may be interrupted at a fraction of the maximum expected load level (e.g. up to about 5 percent (%), up to about 10%, up to about 15%, or up to about 20% of the maximum load) and the cycles 212a-212d may be spaced at small strain increments (e.g. up to about every 0.1 percent strain (%), up to about 0.2%, up to about 0.3%, up to about 0.5%, or up to about 1.0% strain increments) along the load graph 211. FIG. 2C illustrates a graph or plot of a response 213 of the load 110 versus CMOD 208, wherein the CMOD 208 may be measured by the tool 126. The slope 214a-214d of the response is taken at each unloading or cycling point 212a-212d along the response. The inverse of the slope 214a-214d (wherein a slope or group of slopes may be referred to as 214) is referred to as the compliance measurements 216a-216d (wherein a compliance measurement or measurements may be referred to as 216), which may be measured against strain 210a-210d to obtain compliance points 218a-218d as shown in FIG. 2D. In at least one embodiment of the present invention, a separate set of compliance measurements 216 is taken for each flaw 108. Although the illustration depicts three flaws 108, and four cycling points 212, it should be understood that any reasonable number of flaws 108 and cycling points 212 is within the scope of the present invention.

Figure 3:
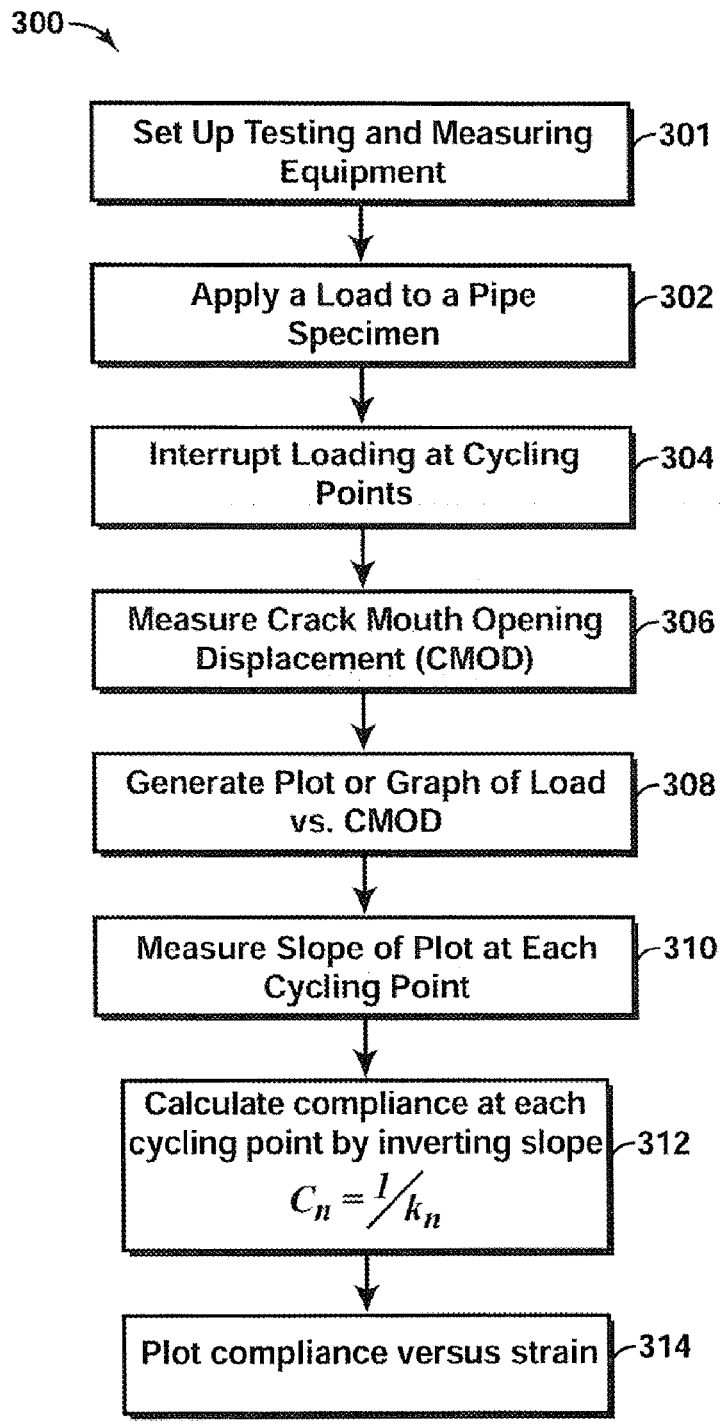
FIG. 3 is an exemplary flow chart of the test procedure and data acquisition of certain aspects of the present invention, which references the experimental configuration of FIGS. 1A-1C and graphical representations of FIGS. 2A-2D.

An exemplary flow chart of the test procedure 300 and data acquisition of certain aspects of the present invention may be viewed at FIG. 3, which references the test configuration of FIGS. 1A-1C and graphical representations of FIGS. 2A-2D. Accordingly, FIG. 3 may be best understood by concurrently viewing FIGS. 1A-1C, and FIGS. 2A-2D. Initially, the testing equipment, such as the pipe specimens 101, 102 and the tool 126 may be configured and calibrated 301. A load 110 may be applied 302 to the pipe specimen 102. The load 110 may be one of longitudinal, torsion, bending, compression, or some combination thereof. Loading may then be interrupted 304 and cycles of loading and unloading applied at certain points along the stress curve 211, called cycling points 212a-212n. The strain 210, the load 110, and the crack mouth opening displacement (CMOD) 208 are measured 306 at each cycling point 212. Then, at least two plots or curves are generated 308: one of load 110 versus CMOD 208 and one of load 110 versus strain 210. The slope of the curve is measured 310 at each cycling point 212 and the compliance is calculated by taking the inverse of the slope 312. Once compliance is calculated, then those values may be plotted or graphed versus strain 314, wherein the compliance versus strain graph is preferably valid beyond the yield point of the specimen.

Preferably, the cycling points are spaced at regular strain intervals, including at least one cycling point 212 in the elastic region of the stress curve 211, at least one cycling point 212 in the near plastic region (or small scale yielding portion) of the stress curve 211, and at least one cycling point 212 in the far plastic region (or large scale yielding portion) of the stress curve 211. More preferably, a greater number of cycling points 212 are utilized rather than fewer cycling points 212, but the number may be limited by time, resources or other practical considerations. Although CMOD is used in this example, note that other measurements such as the J-integral, CTOD, or CTOA may be used.

The compliance points 218 may be referred to as the "measured compliance history" or "experimental compliance data." Obtaining a graph of compliance points 218 may be considered the first component of determining the tearing resistance curve for the tested specimens, which may be used as a tearing resistance curve for a commercial product having a similar member, weld, and flaw geometry of the specimens. In some embodiments of the present invention, it is preferable to calculate the initial compliance level 218a from the first unloading 214a of the specimen 101, 102 at each flaw 108 location prior to any flaw growth. For a pipeline, the initial cycle 212a is preferably conducted during the initial elastic (linear) response of the specimen 101, 102. The initial compliance 214a measured at each flaw 108 location may change due to local variations in material properties or geometry and therefore does not necessarily represent crack growth. The initial compliance 214a measurement may be used to adjust the measured compliance data of each flaw 108 location to a common initial compliance level.

Figures 4A, 4B:
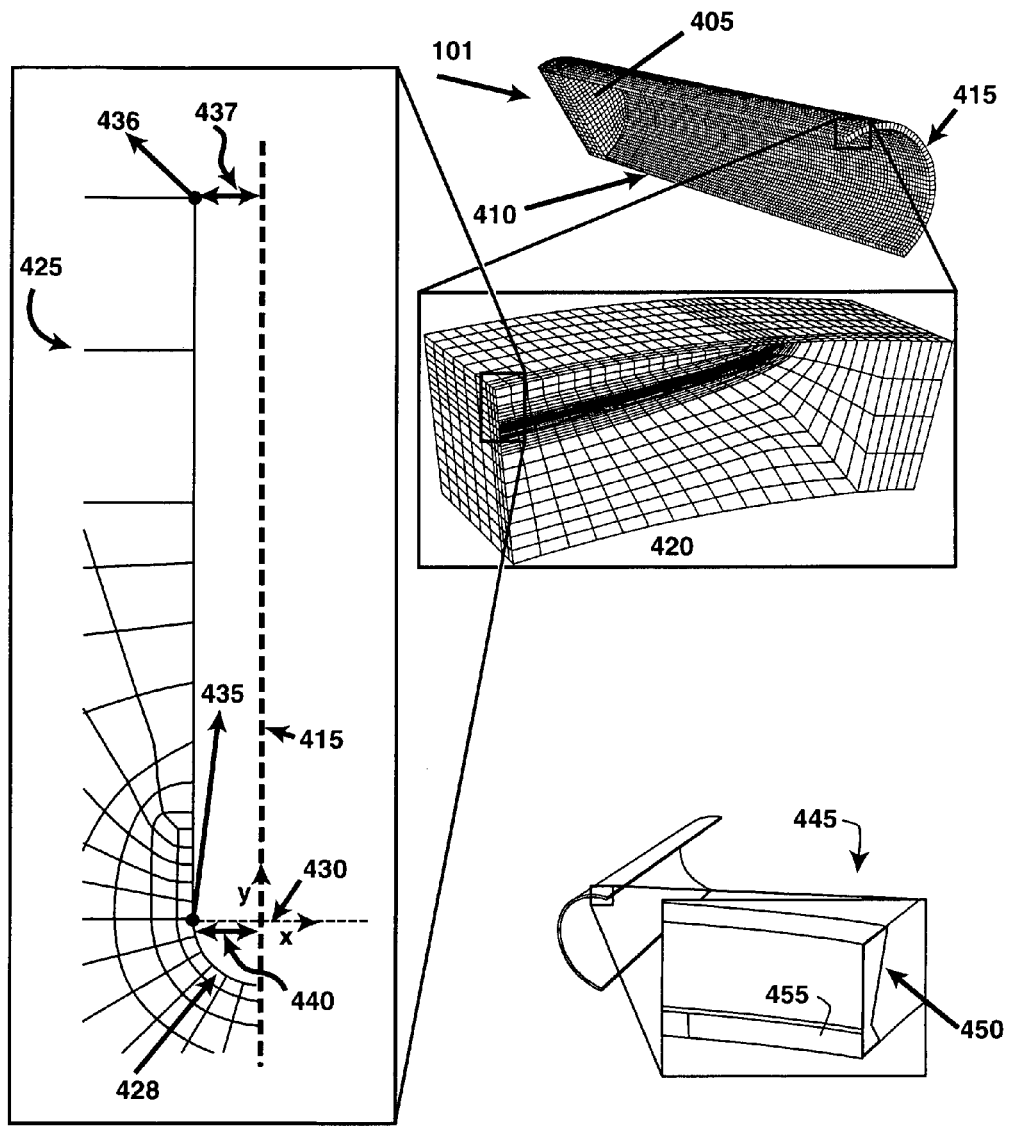
FIGS. 4A-4C are illustrations of exemplary finite element analysis (FEA) representations used to calculate the transfer function relating compliance and flaw height in accordance with certain aspects of the present invention.
Figure 4C:
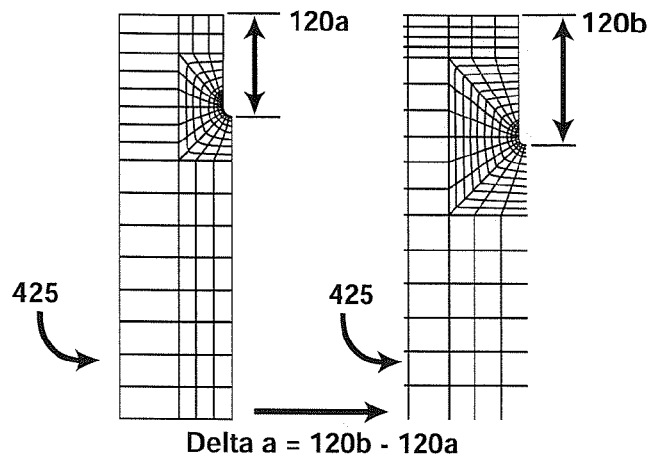

FIGS. 4A-4C are illustrations of exemplary finite element analysis (FEA) representations used to calculate the transfer function relating compliance 216 and flaw height 120 in accordance with certain aspects of the present invention, as described in the discussion of FIGS. 1B, 2A-2D, and 3 above. Accordingly, FIGS. 4A-4C may be best understood by concurrently viewing FIGS. 1B, 2A-2D, and 3 above. In FIG. 4A the pipe specimen 101 is represented by a quarter symmetry model showing an end-cap 405 (used to apply the load 110), symmetry planes 410 and 415, and a close-up of the three-dimensional flaw 420. A flaw profile 425 is also shown. The flaw profile 425 includes a Cartesian frame of reference 430 placed such that the origin of the frame of reference 430 is placed at the center of the flaw tip radius 428 and a node 435 is placed at the point where the flaw tip radius 428 intersects the x-axis of the frame of reference 430. The distance from the node 435 to the center of the flaw tip radius is 440. Another node 436 is placed at the flaw mouth opening and a distance 437 is measured from the point where the center of the flaw tip radius 428 projected along the y-axis to node 436, which is considered the crack mouth opening displacement (CMOD) 208. FIG. 4B shows a quarter symmetry model 445 with a weld 450 and a flaw 455. FIG. 4C illustrates two views of the flaw profile 425 showing a change in flaw height 120 from a first flaw height 120a to a second flaw height 120b.

The FEA may be used to determine the influence of changes of CMOD 208 on the change in compliance measurements 216. The exemplary FEA model preferably uses three-dimensional solid elements. A mesh sensitivity study may be used to determine the correct mesh density to allow the analysis to properly converge and a non-linear plastic material model may also be used in the calculation. The material behavior is preferably determined from the same materials used in the experimental procedure 300.

In exemplary embodiments of the present invention, the symmetry planes 415 and 410 may be used to reduce the size of the model, but a complete model may not include the symmetry planes 410 and 415. Loads 110 are applied to the numerical analysis to duplicate the load cycle applied to the experimental configuration 100. The applied loads may include internal pressure and a displacement load applied to the end cap 405 to place the model in tension. The tension load follows the same load-unload path as discussed in FIG. 2B such as the unloading paths 212 and preferably include loading past the yield point of the specimen. The shape of the flaw 420 preferably represents the actual shape and size of the flaw tested in the experiment 100. The driving force in terms of CTOD (crack tip opening displacement) may be defined as the change in distance 440 due to application of the load 110. The distance 440 is measured between node 435 and the origin of radius 428 projected on the x-axis of reference frame 430. CMOD (crack mouth opening displacement) 208 is defined by a change in distance 437 from the starting configuration before the load 110 is applied. The distance 437 measurement is between node 436 and the y-axis passing through the origin of radius 428 of reference frame 430. The exemplary model shown in FIG. 4A does not contain a weld. However, the same methodology may be used when a weld is present as shown in FIG. 4B. The FEA model may be used in this way to calculate the values of CMOD 208, CTOD and load 110 at multiple data points 212 along the load path 211. Beneficially, these values include the effects of the geometry of the specimen and are valid beyond the yield point of the specimen.

The data calculated by the FEA analysis may be represented as shown in FIGS. 2A-D. More specifically, the load 110 versus strain 210 and the load 110 versus CMOD 208 may be developed. The compliance calculation 216 of the flaw 108 are calculated as the inverse of the slope 214 of the unloading points 212. Additional exemplary FEA models may be developed following similar methods to those described, except that the flaw height 120 is increased as shown in FIG. 4C from 120$a$ to 120$b$. For example, the flaw height 120 may be increased from 3.0 mm to 3.5 mm. The analysis is repeated and the CMOD 208, CTOD and load 110 are calculated along the same load path as shown in FIG. 2B. Similarly, the compliance 216 may be calculated for the flaw height 120 at each unloading point 212 for the corresponding slopes 214. In addition, the FEA could be used to calculate other driving force parameters. For example, most commercially available FEA packages can also calculate a driving force parameter called the J-integral. A definition of the J-integral may be found at ANDERSON, T. L., *Fracture Mechanics: Fundamentals and Applications*, 2d ed., CRC Press, Inc., p. 126 (1995).

Figure 4D:
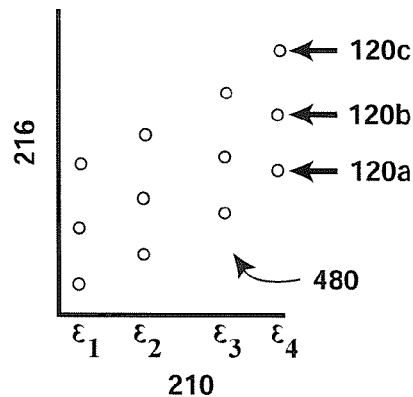
FIGS. 4D-4E are illustrations of exemplary graphical representations of the FEA analysis described in the FEA representations of FIGS. 4A-4C.
Figure 4E:
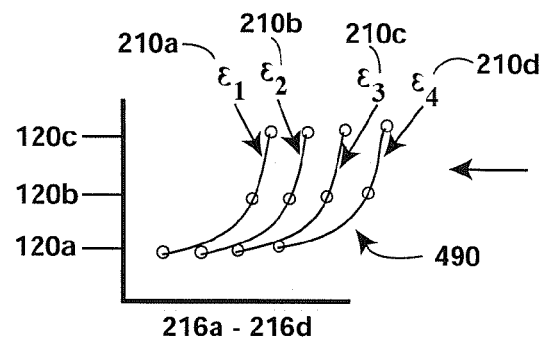

FIGS. 4D-4E are illustrations of exemplary graphical representations of the FEA analysis described in the discussion of FIGS. 4A-4C above. Accordingly, FIGS. 4D-4E may be best understood by concurrently viewing FIGS. 2A-2D, 3, and 4A-4C above. FIG. 4D illustrates an exemplary graph 480 showing compliance 216 versus strain 210 for each flaw height 120$a$-120$c$. FIG. 4E is an exemplary illustration of a graph 490 of compliance 216 versus flaw height 120$a$-120$c$ showing lines of constant strain 210$a$-210$d$.

In some embodiments of the present invention, the graph 490 may be called the "compliance to crack depth transfer function" (referred to herein as the "transfer function") 490. The transfer function 490 of the specimen may be used to convert experimentally obtained compliance data 216 to flaw height 120 by interpolating between the lines of constant strain 210$a$-210$d$. The exemplary embodiments of the present invention capture the influence of plasticity at large strains on the compliance 216 measurement. In some embodiments, the transfer function 490 is developed, which captures the influence of strain 210 and flaw geometry on the compliance 216 of a structure, such as a pipe. Preferably, the transfer function 490 may then be used to estimate flaw height 120 of the experimentally obtained compliance data 216 at each level of strain 210. Another transfer function 490 may be developed to estimate flaw length 440 of the experimentally obtained compliance data 216 at each level of strain 210. Note that this transfer function remains valid beyond the yield point of the specimen.

FIGS. 5A-5D are illustrations of exemplary graphical representations of numerical analyses showing calculation of a tearing resistance curve 512 in accordance with certain aspects of the present invention, as described in the discussion of FIGS. 1A-1C, 2A-2D, 3, and 4A-4B above. Accordingly, FIGS. 5A-5D may be best understood by concurrently viewing FIGS. 1A-1C, 2A-2D, 3, and 4A-4B above. In FIG. 5A an exemplary application of the transfer function 490 is shown such that the compliance 216 measured during an experiment is transferred to flaw height 120 as a function of applied strain 210 giving the flaw height history 502 of the specimen 101, 102. FIG. 5B shows a graph of a fracture parameter 506 versus strain 210. The fracture parameter 506 may be the J-integral, the CTOD, or some other known driving force parameter. The fracture parameter 506 may be calculated from a FEA such as the one described with reference to FIGS. 4A-4C. The preferred method of the present invention is to use CTOD as calculated in the FEA as the fracture parameter 506. FIG. 5C illustrates an exemplary graph of the applied fracture driving force 508 as a function of strain 210. FIG. 5D illustrates an exemplary graph of the tearing resistance curve 512, shown by the fracture driving force (CTOD) 508 as a function of flaw or crack growth 510.

In some embodiments of the present invention, the tearing resistance curve 512 is developed from the experimental flaw height history 502, calculated from the transfer function 480, 490, the experimentally measured compliance 218, and the numerically produced fracture parameter 506 as a function of strain 210. A point on graph 502 gives a flaw height of 120$b$ versus a strain of 210$b$. The curve corresponding to flaw height 120$b$ is used in FIG. 5B to determine the fracture parameter at a strain of 210$b$. This process is repeated for all the data points on plot 502. After the corresponding fracture parameter 506 for each pair of flaw height 120$a$-120$n$/strain 210$a$-210$n$ data points are determined a plot 508 of fracture parameter 506 versus strain 210 can be developed as shown in FIG. 5C. Similarly, after the corresponding fracture parameter 506 for each pair of flaw height 120$a$-120$n$ and strain point 210$a$-210$n$ of plot 502 is determined, the fracture parameter 506 versus change in flaw height 510 can be produced. Change in flaw height 510 is calculated by subtracting the initial flaw height 120 (starting flaw height in the experimental specimen 101, 102) from the flaw height calculated in plot 502.

EXPERIMENTAL EXAMPLES

Figure 6A:
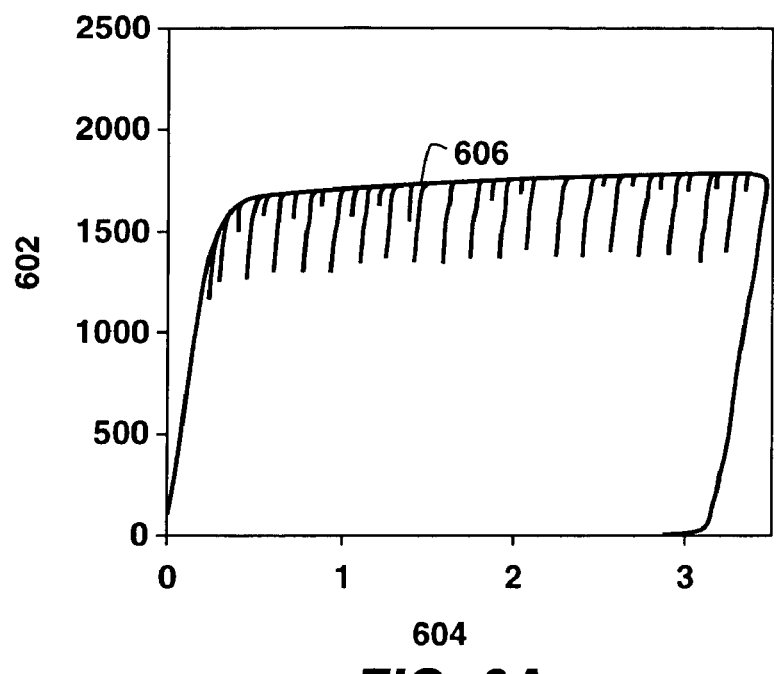
FIGS. 6A-6U are illustrations of results of an experimental application of certain aspects of an exemplary embodiment of the present invention.
Figure 6B:
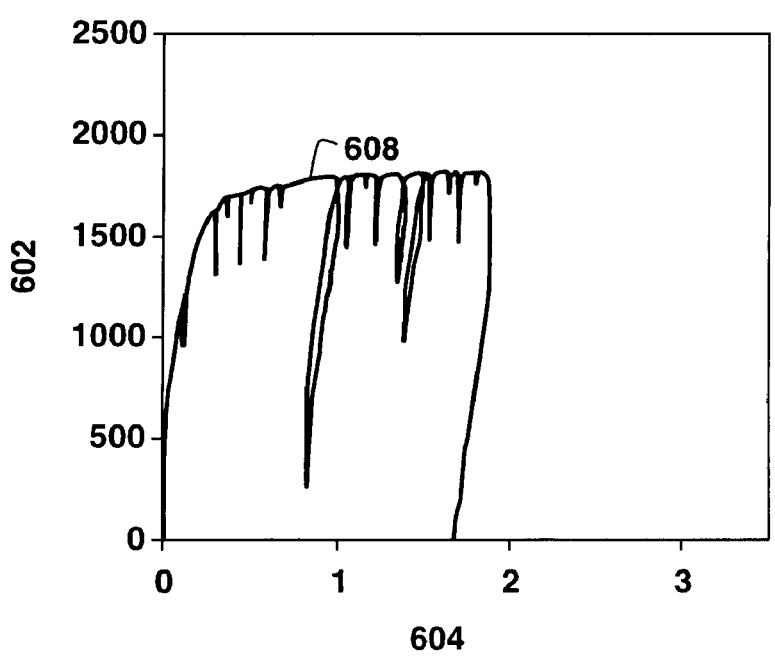
Figure 6C:
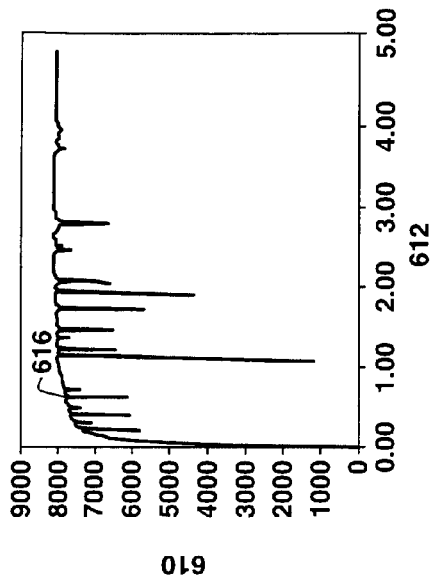
Figure 6D:
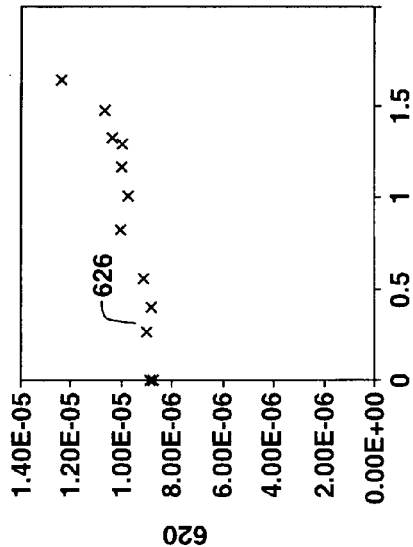
Figure 6E:
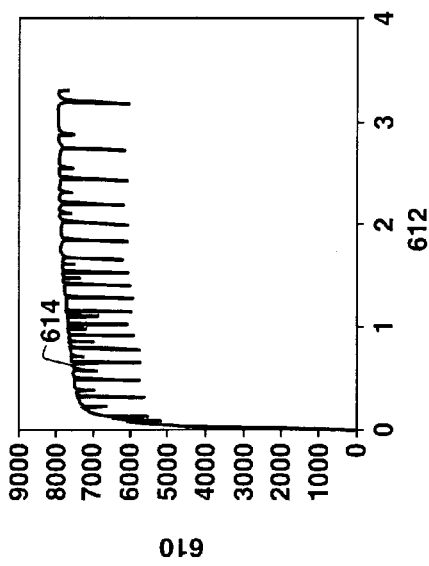
Figure 6F:
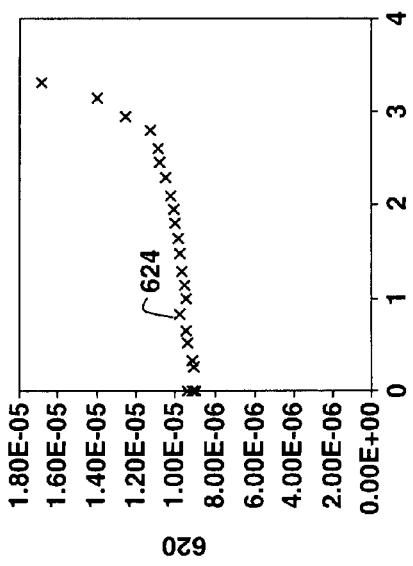
Figure 6G:
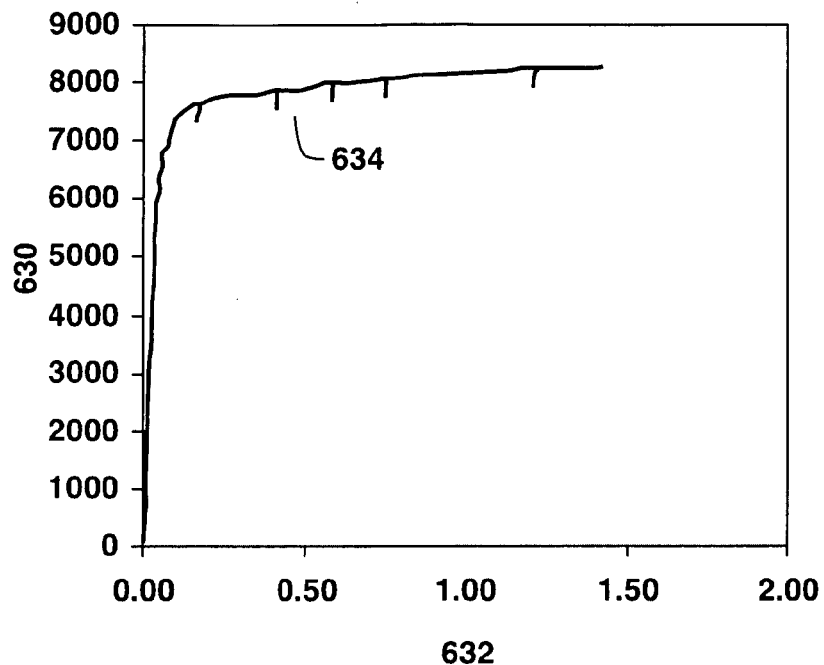
Figure 6H:
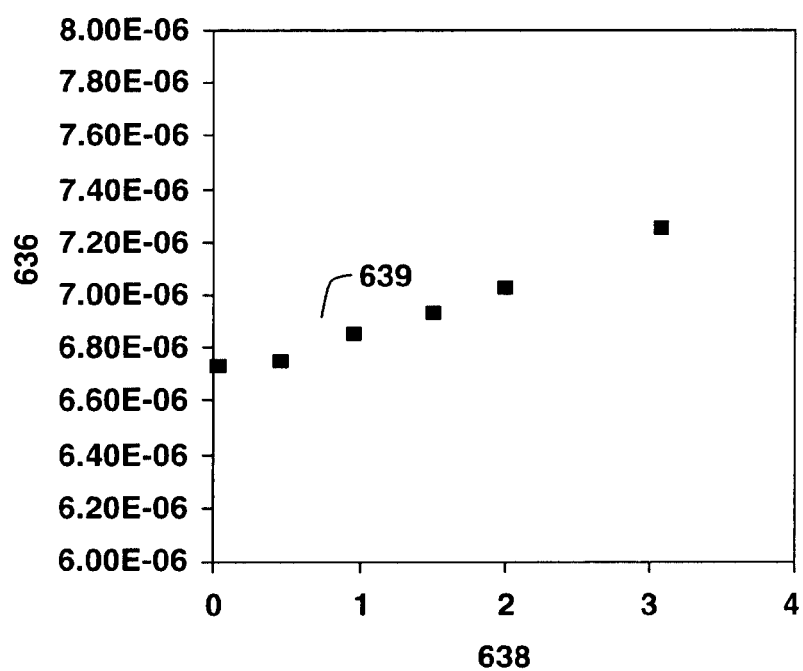
Figure 6L:
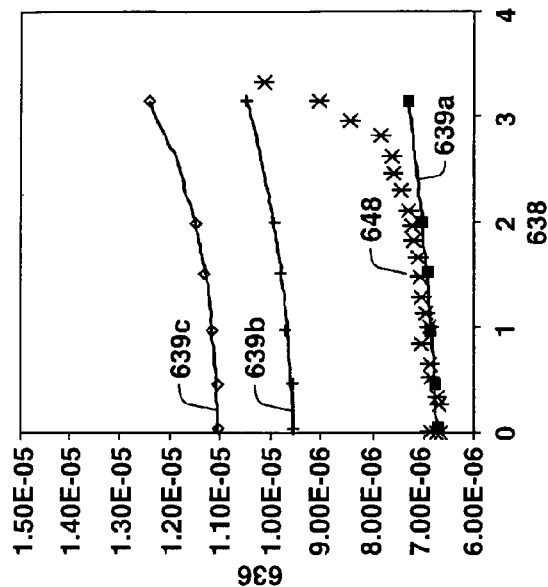
Figure 6M:
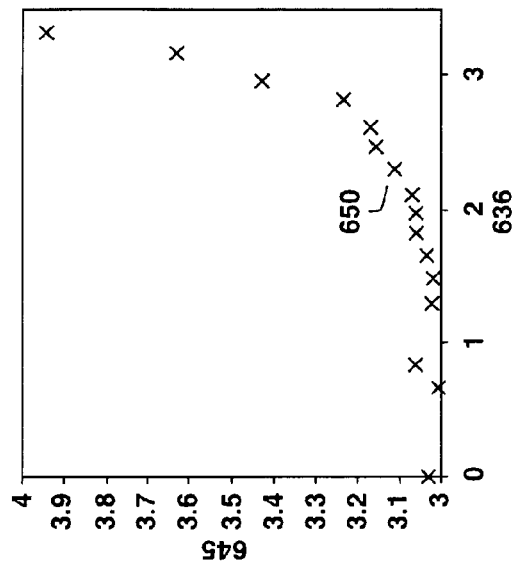
Figure 6N:
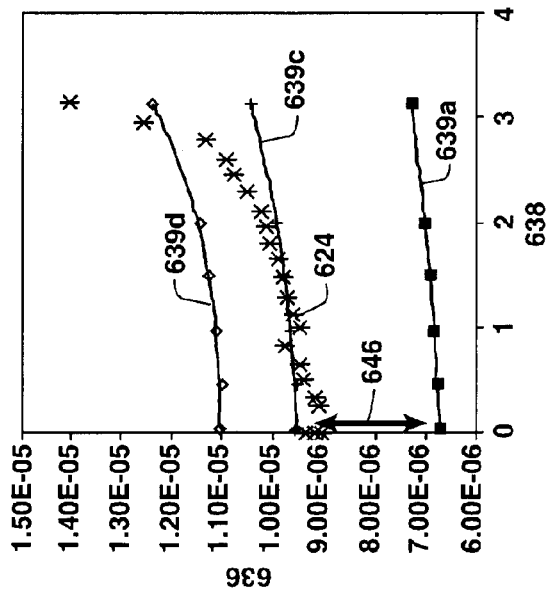
Figure 6O:
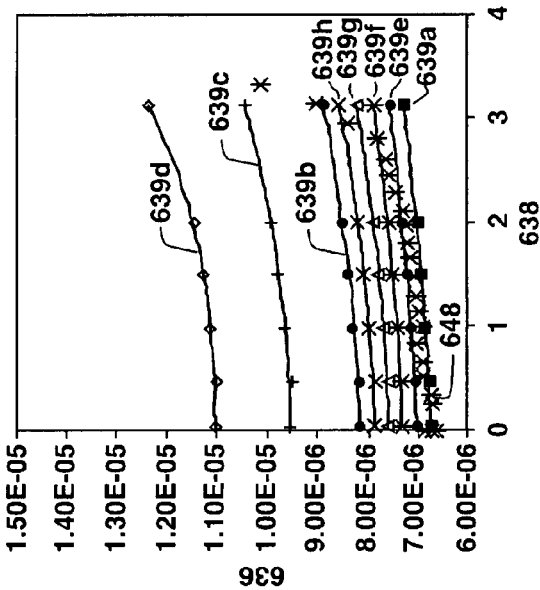
Figure 6P:
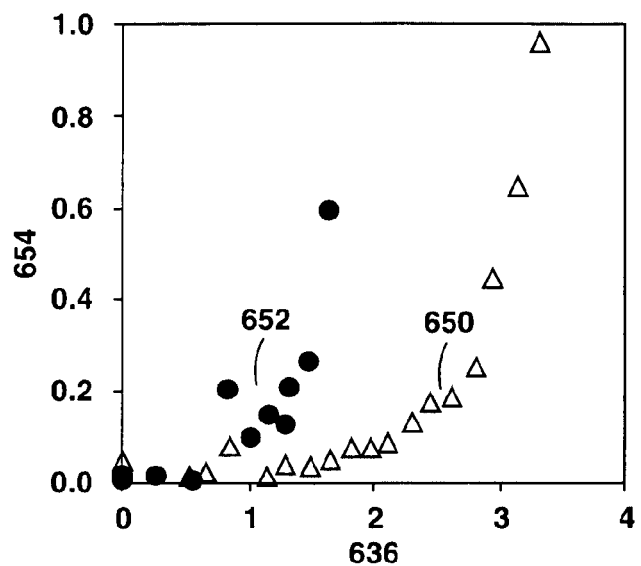
Figure 6Q:
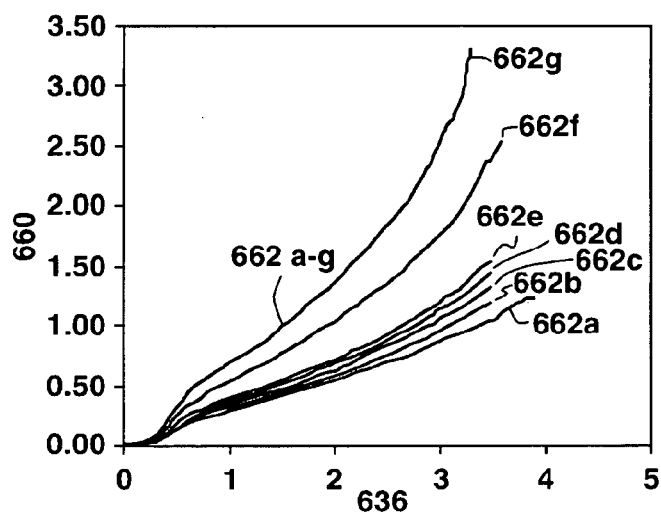
Figure 6R:
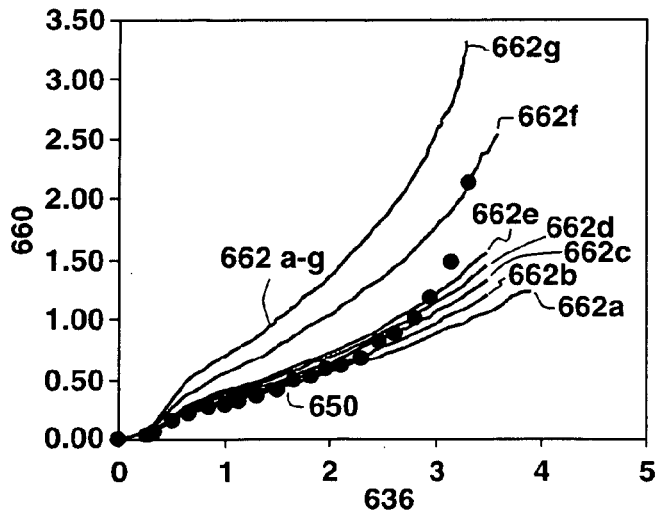
Figure 6S:
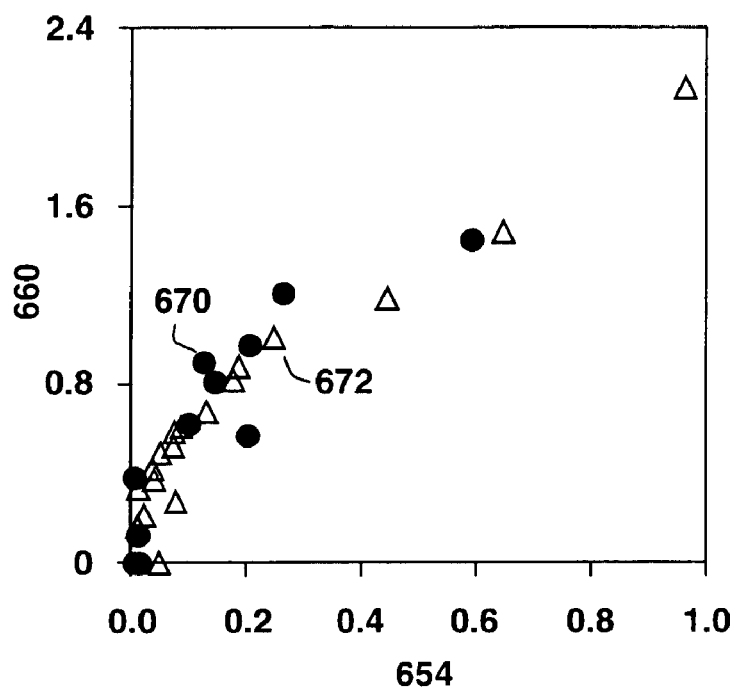
Figure 6T:
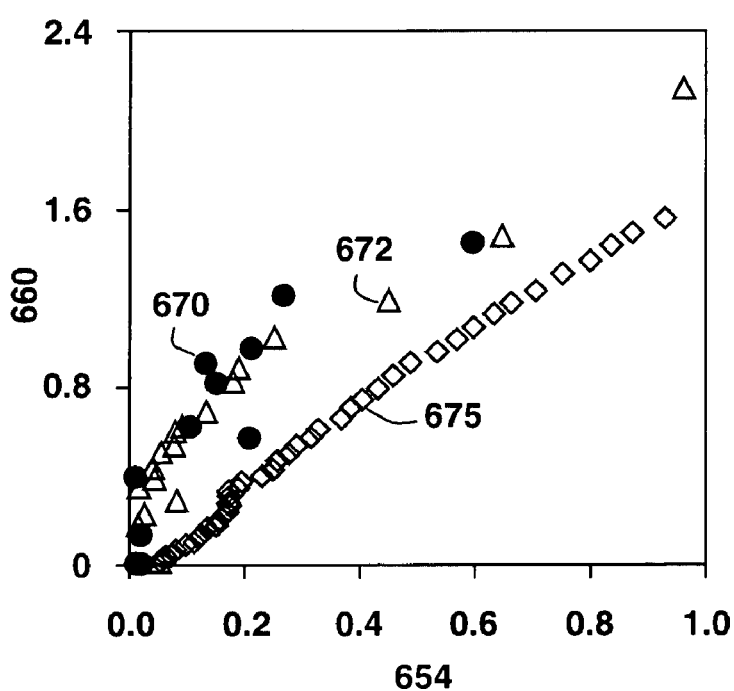
Figure 6U:
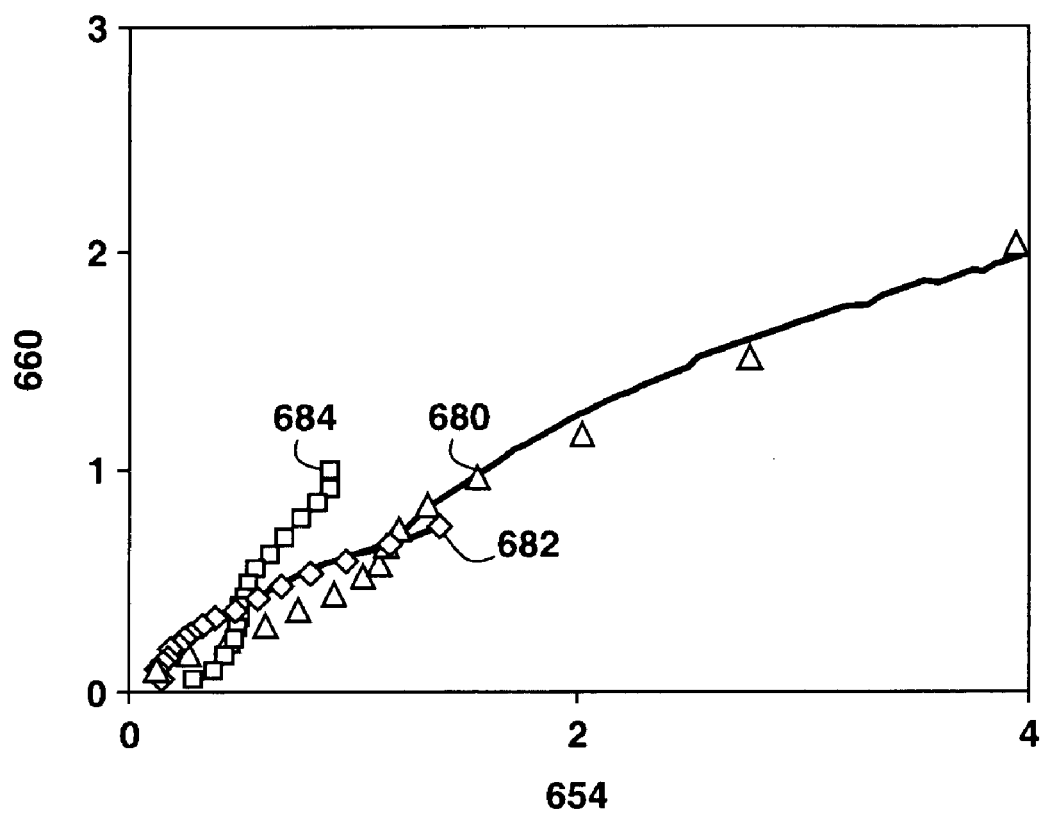

FIGS. 6A-6U are illustrations of results of an experimental applications of certain aspects of an exemplary embodiment of the present invention, as described in the discussion of FIGS. 1A-1C, 2A-2D, 3, 4A-4E, and 5A-5D above. Accordingly, FIGS. 6A-6U may be best understood by concurrently viewing FIGS. 1A-1C, 2A-2D, 3, 4A-4E, and 5A-5D.

Example 1

A first experimental test program was conducted on an API (American Petroleum Institute) X-65 grade pipe with an outer diameter of 12.75 inches and a nominal wall thickness of 0.562 inches. This pipe was selected for its wide use in hydrocarbon recovery and well-based operations, but the tests described herein are applicable to a wide variety of tubulars and other structural members such as I-beams, catenary risers, etc. The test program consisted of two tests on two pipe segments. There was no weld in the pipes. Multiple flaws were machined on the outer surface of the pipe segments. The flaws machined in the pipe segments were of the same size, 3 millimeters (mm) in height and 50 mm long. The test could also be conducted with only one flaw, or many flaws machined on the internal surface of the pipe. The flaws were machined in a plane perpendicular to the load direction and were surface breaking flaws.

The first pipe segment was pressurized to an internal pressure of 200 pounds per square inch (psi) and the second pipe segment was pressurized to a pressure of 5,700 psi. Both pipe segments were loaded in displacement control and approximately followed the cyclic load path suggested in FIG. 2B (non-uniformly cycled at approximately every 0.25% of strain). FIGS. 6A-6B are graphs of load 602 (measured in kilo-pounds per square inch (kpsi)) versus strain 604 (measured in percent displacement (% disp.)) and show the measured load history for the low pressure pipe segment 606 and the measured load history for the high pressure pipe segment 608. FIGS. 6C-6D are graphs of load 610 (measured in kilo-Newtons (kN)) versus CMOD 612 (measured in millimeters (mm)) and show the measured response for the low pressure pipe segment 614 and the measured response for the high pressure pipe segment 616. As seen from FIGS. 6A-6D the measurements are taken beyond the yield point of the specimen.

Once the measured test results were collected, the compliance of each pipe segment was calculated in accordance with the methodology described in FIGS. 2A-2D. FIGS. 6E-6F are graphs of compliance 620 (measured in millimeters/kilo-Newton (mm/kN)) versus strain 622 (measured in % disp.) and show the measured compliance for the low pressure pipe segment 624 and the high pressure pipe segment 626. FIG. 6G shows a curve 634 plotting load 630 (kN) versus CMOD 632 (mm) generated by a finite element analysis (FEA) model constructed according to the outline set forth in FIGS. 4A-4C with a 3 mm flaw. FIG. 6H shows a compliance curve 639 plotting compliance 636 (mm/kN) versus strain 638 (%) calculated in accordance with the techniques described in FIG. 2C. FIG. 6I shows a compilation of compliance curves, where curve 639$a$ is the compliance curve for a 3 mm flaw, 639$b$ is the compliance curve for a 3.5 mm flaw, 639$c$ is the compliance curve for a 4.0 mm flaw, and 639$d$ is the compliance curve for a 4.5 mm flaw. FIG. 6J shows curves plotting flaw height 645 (mm) versus compliance 636 (mm/kN) along lines of constant strain, where curves 639$a$, 639$b$, 639$c$, and 639$d$ are re-plotted as functions of constant strain such that 643$a$ has a strain of 0.04%, 643$b$ has a strain of 1.51%, and 643$c$ has a strain of 3.14%.

To reduce the number of FEA models, the data on plot 6J were curve fitted as functions of constant strain. Here, a fitted polynomial function of order 3 was used to fit the lines. However, other curve fitting approaches may be used to best fit the data of other pipe geometries such as a linear curve fit or an exponential curve fit. FIG. 6K shows the compliance transfer function of FIG. 6I with additional functions interpolated from the fitted data of FIG. 6J for different flaw heights. Curve 639$e$ is the compliance prediction curve for a 3.1 mm flaw height, 639$f$ is for a flaw height of 3.2 mm, curve 639$g$ is for a flaw height of 3.3 mm, and curve 639$h$ is for a flaw height of 3.4 mm. Additional transfer functions at more varied flaw heights 120 may be developed as needed by interpolation or alternate methods. One alternative method of obtaining compliance curves for the various flaw heights 645 is to produce FEA models of each of the additional flaw heights 645. FIG. 6L combines the compliance curves 639$a$, 639$c$, 639$d$ with the measured compliance for the low pressure pipe segment 624, wherein the first three experimental data points are offset from the FEA calculated compliance of a 3 mm deep flaw by an amount termed the "structural compliance" 646. FIG. 6M shows the compliance curve 648 resulting from calibrating the experimental data such that the average of the first three data points of curve 624 correspond to the first data point of curve 639$a$. FIG. 6N shows the calibrated compliance curve 648 superimposed over the FEA produced compliance curves from FIG. 6K. FIG. 6O shows the experimental crack growth history 650 in terms of flaw height 645 (mm) versus strain 636 (%) resulting from applying the compliance transfer function 639$a$-639$h$ to the calibrated compliance curve 648. FIG. 6P shows the low pressure (200 psi) experimental crack growth history 650 and high pressure (5,700 psi) experimental crack growth history 652 in terms of change in flaw depth 654 (mm) versus strain 636 (%). The steps used to determine the low pressure experimental crack growth history 650 may be used to determine the high pressure experimental crack growth history 652.

After determining the high pressure and low pressure experimental crack growth histories 650, 652, the driving force or fracture parameter 506 may be calculated as a function of strain 636 and crack growth (change in flaw height 645). A finite element model may be produced according to the methods outlined in FIGS. 4A-4B and FIGS. 5A-5D. FIG. 6Q shows the FEA produced curves 662$a$-662$g$ plotting CTOD 660 (mm) as a function of strain 636 (%) for various flaw sizes: curve 662$a$—3.0 mm, 662$b$—3.1 mm, 662$c$—3.2 mm, 662$d$—3.3 mm, 662$e$—3.4 mm, 662$f$—4.0 mm, and 662$g$—4.5 mm. The experimental crack growth history 650 shown in FIG. 6O is re-plotted on FIG. 6R with the FEA produced curves 662$a$-662$g$. The corresponding driving force 506 for each experimental flaw height 645 can be obtained by combining 650 and 662$a$-662$g$. This experimental data can now be replotted as shown in FIG. 6S as CTOD as a function of change in crack growth 654 (mm). Also plotted are the results from the test with a pressure of 5,700 psi. The results shown in FIG. 6S show that the addition of pressure has only a small affect on the resistance curve for the tested API X-65 material. FIG. 6T shows the tearing resistance curves 670 and 672 measured on a full-scale test of the present invention compared to the tearing resistance curve 675 measured using a standard SENB (single edge notched bend) specimen.

Example 2

A second experimental test program was conducted on a pipe containing a girth weld. The pipe diameter was 12.75 inches and the pipe was similar to that used in experimental example 1. A pulse gas metal arc welding process was used to produce the weld. The flaws were spaced 120 degrees apart and placed in the center of the weld on the outside diameter surface of the weld. Each flaw was instrumented with crack mouth opening displacement gages. A full-scale tension test was conducted on the pipe sample. The weld yield strength was approximately 5% greater than the pipe material yield strength. Using the same procedures described in experimental example 1, the un-loading compliance technique was used to measure the tearing resistance curve at each flaw location. Since three flaws were instrumented during the test, three resistance curves were measured.

FIG. 6U shows the plot of the resistance curves 680, 682, and 684 measured from the three flaws included in the test. Curve 680 relates to flaw 1, curve 682 shows the resistance curve for flaw 2, and curve 684 for flaw 3. The variation in observed tearing resistance is due to variations in the material toughness properties. The lowest resistance curve 680 represents the worst fracture toughness between the three flaw locations measured.

In another alternative embodiment, the data acquisition, curve fitting, FEA analysis and other functions may be performed with a processing device, such as a computer, server, database or other processor-based device. The processing device may include an application that interacts with a user. The application may be implemented as a spreadsheet, program, routine, software package, or additional computer readable software instructions in an existing program, which may be written in a computer programming language, such as Visual Basic, Fortran, C++, Java and the like. Of course, the processing device may include memory, such as hard disk drives, floppy disks, CD-ROMs and other optical media, magnetic tape, and the like, for storing the application. The processing device may include a monitor, keyboard, mouse and other user interfaces for interacting with a user.

As an example of the operation of the processing device, the user may utilize an application to specify the flaw height 120, flaw length 440, and other flaw and specimen sizes and shapes in the FEA analysis. The user may further input a constitutive description of a weld, member, or specimen material. Materials information may again be provided from a user or provided from the application for selection by the user from a list of available materials (i.e. through a graphical user interface or in an Excel spreadsheet). Once determined, the tearing resistance of the specimen may be provided to a user via a display or a report.

While the present invention may be susceptible to various modifications and alternative forms, the exemplary embodiments discussed above have been shown by way of example. However, it should again be understood that the invention is not intended to be limited to the particular embodiments disclosed herein. Indeed, the present invention is to cover all modifications, equivalents, and alternatives falling within the spirit and scope of the invention as defined by the following appended claims.

What is claimed is:

1. A method of obtaining a representative tearing resistance curve of a commercial member, comprising:
   conducting a full scale fracture mechanics test of a specimen having a specimen geometry of a representative size and shape of the commercial member and at least one specimen flaw having a specimen flaw geometry of a representative size and shape of a flaw in the commercial member, wherein the full scale fracture mechanics test provides at least two results; and
   generating a tearing resistance curve of the specimen utilizing the at least two results of the full scale fracture mechanics test, wherein the tearing resistance curve of the specimen is representative of a tearing resistance curve of the commercial member and is dependent upon at least the size and shape of the specimen geometry and the size and shape of the specimen flaw geometry.

2. The method of claim 1, wherein at least one of the at least two results is a load-displacement curve, wherein the load-displacement curve is measured beyond a yield point of the specimen.

3. The method of claim 1, wherein the full scale fracture mechanics test comprises loading the specimen past the specimen's yield point.

4. The method of claim 1, wherein the full scale fracture mechanics test further comprises a weld having a weld geometry of a representative size and shape of a weld in the commercial member.

5. The method of claim 1, wherein the specimen is comprised of a material having representative material properties of the commercial member.

6. The method of claim 1, wherein the specimen is the same size and shape of the commercial member.

7. The method of claim 1, wherein the specimen is a one half scale model of the commercial member.

8. The method of claim 1, wherein the commercial member is a pipe segment.

9. The method of claim 1, wherein the flaws are generated by a machining process.

10. The method of claim 1, wherein the full scale fracture mechanics test further comprises cyclically loading the specimen at a plurality of load increments up to the failure point of the specimen.

11. The method of claim 10, wherein the cyclic loading is one of longitudinal, bending, torsional, compressive, and any combination thereof.

12. The method of claim 10, wherein the at least two results are load on the specimen and crack mouth opening displacement of the at least one specimen flaw.

13. The method of claim 12, wherein the at least two results further includes strain of the specimen.

14. The method of claim 13, further comprising plotting a curve of the load on the specimen versus the crack mouth opening displacement of the at least one specimen flaw, and calculating the slope of the curve at each cyclical loading.

15. The method of claim 14, further comprising:
   calculating a measured compliance of the specimen by calculating the inverse of the slope of the curve at each cyclical loading; and
   developing at least one transfer function between the measured compliance of the specimen and the at least one specimen flaw height, wherein the at least one transfer function utilizes at least one compliance measurement from between the yield point of the specimen and the failure point of the specimen.

16. The method of claim 15, wherein finite element analysis is utilized to develop the at least one transfer function.

17. The method of claim 15, further comprising:
   utilizing the at least one transfer function to calculate a fracture driving force of the specimen as a function of strain of the specimen; and
   plotting the fracture driving force as a function of change in the at least one specimen flaw height to determine a tearing resistance curve of the specimen.

18. The method of claim 17, wherein the fracture driving force is represented by a fracture parameter.

19. The method of claim 18, wherein the fracture parameter is one of J-integral and crack tip opening displacement (CTOD).

20. The method of claim 19, wherein the tearing resistance curve of the specimen is represented by one of: a plot of crack tip opening displacement (CTOD) versus change in the at least one specimen flaw height, J-integral versus change in the at least one specimen flaw height, crack mouth opening displacement (CMOD) versus change in the at least one specimen flaw height, or crack tip opening angle (CTOA) versus change in the at least one specimen flaw height.

21. A method of producing hydrocarbons, comprising:
designing a pipeline for producing hydrocarbons, wherein the pipeline comprises a commercial pipe segment, wherein the commercial pipe segment is selected utilizing a representative tearing resistance curve of the commercial pipe segment, wherein obtaining the representative tearing resistance curve of the commercial pipe segment comprises:
conducting a full scale fracture mechanics test of a specimen having a specimen geometry of a representative size and shape of the commercial pipe segment and at least one specimen flaw, the specimen flaw having a specimen flaw geometry of a representative size and shape of a flaw in the commercial pipe segment, wherein the full scale fracture mechanics test provides at least two results; and
generating a tearing resistance curve of the specimen utilizing the at least two results of the representative fracture mechanics test, wherein the tearing resistance curve of the specimen is representative of a tearing resistance curve of the commercial pipe segment and is dependent upon at least the size and shape of the specimen geometry and the size and shape of the specimen flaw geometry; and
producing hydrocarbons utilizing the pipeline.

22. The method of claim 21, wherein at least one of the results is a load-displacement ratio, wherein the load-displacement ratio result is measured beyond a yield point of the specimen.

23. The method of claim 21, wherein the full scale fracture mechanics test further comprises a weld having a weld geometry of a representative size and shape of a weld in the commercial pipe segment.

24. The method of claim 21, wherein the specimen is comprised of a material having representative material properties of the commercial pipe segment.

25. The method of claim 21, wherein the specimen is the same size and shape of the commercial pipe segment.

26. The method of claim 21, wherein the specimen is a one half scale model of the commercial pipe segment.

27. The method of claim 21, wherein the full scale fracture mechanics test further comprises cyclically loading the specimen at a plurality of load increments up to the failure point of the specimen.

28. The method of claim 27, wherein the at least two results include load on the specimen and crack mouth opening displacement of the at least one specimen flaw.

29. The method of claim 27, wherein the cyclic loading is one of longitudinal, bending, torsional, compressive, and any combination thereof.

30. A structure, comprising:
a commercial member, wherein the commercial member is selected utilizing a representative tearing resistance curve of the commercial member, wherein obtaining the representative tearing resistance curve of the commercial member comprises:
conducting a full scale fracture mechanics test of a specimen having a specimen geometry of a representative size and shape of the commercial member and at least one specimen flaw, the specimen flaw having a specimen flaw geometry of a representative size and shape of a flaw in the commercial member, wherein the full scale fracture mechanics test provides at least two results; and
generating a tearing resistance curve of the specimen utilizing the at least two results of the representative fracture mechanics test, wherein the tearing resistance curve of the specimen is representative of a tearing resistance curve of the commercial member and is dependent upon at least the size and shape of the specimen geometry and the size and shape of the specimen flaw geometry.

31. The structure of claim 30, wherein at least one of the results is a load-displacement ratio, wherein the load-displacement ratio result is measured beyond a yield point of the specimen.

32. The structure of claim 30, wherein the full scale fracture mechanics test further comprises a weld having a weld geometry of a representative size and shape of a weld in the commercial member.

33. The structure of claim 30, wherein the specimen is comprised of a material having representative material properties of the commercial member.

34. The structure of claim 30, wherein the specimen is the same size and shape of the commercial member.

35. The structure of claim 30, wherein the specimen is a one half scale model of the commercial member.

36. The structure of claim 30, wherein the commercial member is a pipe segment.

37. The structure of claim 30, wherein the full scale fracture mechanics test further comprises cyclically loading the specimen at a plurality of load increments up to the failure point of the specimen.

38. The structure of claim 37, wherein the at least two results include load on the specimen and crack mouth opening displacement of the at least one specimen flaw.

39. The structure of claim 37, wherein the cyclic loading is one of longitudinal, bending, torsional, compressive, and any combination thereof.

40. An apparatus, comprising:
a processor; and
a memory coupled to the processor, wherein the processor is configured to execute computer readable instructions to:
calculate a measured compliance of a specimen from at least two test results, wherein the test results are obtained by conducting a full scale fracture mechanics test of the specimen having a specimen geometry of a representative size and shape of a commercial member and at least one specimen flaw, the specimen flaw having a specimen flaw geometry of a representative size and shape of a flaw in the commercial member;
develop at least one transfer function between the measured compliance of the specimen and an at least one specimen flaw height;
utilize the at least one transfer function to calculate a fracture driving force of the specimen as a function of strain of the specimen; and
graph the fracture driving force as a function of change in the at least one specimen flaw height to determine a tearing resistance curve of the specimen.

41. The apparatus of claim 40, wherein the at least one transfer function is developed using finite element analysis.

42. The apparatus of claim 40, wherein developing the at least one transfer function utilizes at least one compliance measurement from between the yield point of the specimen and the failure point of the specimen.

43. The apparatus of claim 40, wherein the fracture driving force is represented by a fracture parameter.

44. The apparatus of claim 40, wherein the fracture parameter is one of J-integral and crack tip opening displacement (CTOD).

45. The apparatus of claim 40, wherein the commercial member is a pipe segment.

46. The apparatus of claim 40, wherein the full scale fracture mechanics test further comprises cyclically loading the specimen at a plurality of load increments up to the failure point of the specimen.

47. The apparatus of claim 46, wherein the at least two results include load on the specimen and crack mouth opening displacement of the at least one specimen flaw.

48. The apparatus of claim 47, further comprising graphing a curve of the load on the specimen versus the crack mouth opening displacement of the at least one specimen flaw, and calculating the slope of the curve at each cyclical loading.

49. The apparatus of claim 48, further comprising determining the measured compliance of the specimen by calculating the inverse of the slope of the curve at each cyclical loading.

50. A method of obtaining a tearing resistance curve of a commercial member, the method comprising:
 obtaining at least two results from a full scale fracture mechanics test of a specimen having a specimen geometry of a representative size and shape of the commercial member and at least one specimen flaw, the specimen flaw having a specimen flaw geometry of a representative size and shape of a flaw in the commercial member, wherein the full scale fracture mechanics test includes;
 calculating a measured compliance of the specimen utilizing the at least two results from the full scale fracture mechanics test; and
 developing at least one transfer function between the measured compliance of the specimen and the at least one specimen flaw height, wherein the at least one transfer function utilizes at least one compliance measurement from past the yield point of the specimen.

51. The method of claim 50, wherein the commercial member is a pipe segment.

52. The method of claim 50, wherein the at least one transfer function is developed using finite element analysis.

53. The method of claim 50, wherein the full scale fracture mechanics test further comprises cyclically loading the specimen at a plurality of load increments up to the failure point of the specimen.

54. The method of claim 50, wherein the at least two results include load on the specimen and crack mouth opening displacement of the at least one specimen flaw.

55. The method of claim 50, wherein the specimen includes a weld having a weld geometry of a representative size and shape of the commercial member.

* * * * *